United States Patent
Sigman et al.

(10) Patent No.: US 8,063,359 B2
(45) Date of Patent: Nov. 22, 2011

(54) SYSTEMS AND METHODS FOR IDENTIFYING SUBSTANCES CONTAINED IN A MATERIAL

(75) Inventors: Michael E Sigman, Oviedo, FL (US); Mary R Williams, Eustis, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 369 days.

(21) Appl. No.: 12/244,281

(22) Filed: Oct. 2, 2008

(65) Prior Publication Data

US 2009/0090857 A1 Apr. 9, 2009

Related U.S. Application Data

(60) Provisional application No. 60/978,208, filed on Oct. 8, 2007.

(51) Int. Cl.
*H01J 49/26* (2006.01)
*B01D 59/44* (2006.01)
(52) U.S. Cl. .......................... 250/282; 702/27
(58) Field of Classification Search .......... 250/282; 702/27
See application file for complete search history.

(56) References Cited

U.S. PATENT DOCUMENTS

| | | | |
|---|---|---|---|
| 2,400,557 A | 5/1946 | Lawlor | |
| 6,444,979 B1 * | 9/2002 | Watanabe | 250/282 |
| 7,022,980 B2 * | 4/2006 | Zavitsanos et al. | 250/282 |
| 7,425,700 B2 * | 9/2008 | Stults et al. | 250/282 |

FOREIGN PATENT DOCUMENTS

GB 2410800 8/2005

OTHER PUBLICATIONS

Geert Van Marlen, et al., "Information Theory Applied to Selection of Peaks for Retrieval of Mass Spectra", ACS Publications, Analytical Chemistry, May 1, 2002, pp. 594-598.
Stanley L. Grotch, "Matching of Mass Spectra When Peak Height is Encoded to One Bit", ACS Publications, Analytical Chemistry, May 1, 2002, pp. 1213-1222.
Sigman, et al., "Ignitable Liquid Classification and Identification using the Summed-Ion Mass Spectrum", Instrumentation Science and Technology, 36: 375-393, 2008.
Gan, F., et al. "A novel approach to the retrieval of mass spectrum of a mixture", Analytical Sciences 2000, vol. 16, pp. 603-607.
Hallgren, B., et al. "Quantitative mass spectrometric analysis of mixtures of unsaturated and saturated fatty acids", Acta Chemica Scandinavica 1957, vol. 11, p. 1064.
Yates, Jr., III, "Database searching using mass spectrometry data", Electrophoresis 1998, vol. 19(6), p. 893.
Kang, H.D., et al., "Decomposition of multicomponent mass spectra using Bayesian probability theory", Journal of Mass Spectrometry 2002, vol. 37 (7), pp. 1-18.

(Continued)

*Primary Examiner* — Jack Berman
(74) *Attorney, Agent, or Firm* — Thomas, Kayden, Horstemeyer & Risley, LLP

(57) ABSTRACT

In one embodiment, a system and a method relate to generating a summed ion spectrum for a test sample, the summed ion spectrum identifying ion intensities at multiple different mass-to-charge ratios, and comparing the summed ion spectrum of the test sample with multiple reference summed ion spectra to identify a potential match.

27 Claims, 5 Drawing Sheets

OTHER PUBLICATIONS

Zarrabi, et al., "Use of principal component regression to characterize a complex oxidation product mixture", Journal of Analytical and Applied Pyrolysis, vol. 21, Issue 1-2, 1991, pp. 1-14.

Fraser, et al., "Mass Spectra and Molecular Structure, Part II. The analysis of Mixtures", International Journal of Mass Spectrometry and Ion Physics, vol. 2, Issue 3, 1969, pp. 265-285.

* cited by examiner

SYSTEMS AND METHODS FOR IDENTIFYING SUBSTANCES CONTAINED IN A MATERIAL

CROSS-REFERENCE TO RELATED APPLICATION

This application claims priority to copending U.S. provisional application entitled, "Systems And Methods For Identifying Substances Contained In A Material," having Ser. No. 60/978,208, filed Oct. 8, 2007, which is entirely incorporated herein by reference.

NOTICE OF GOVERNMENT-SPONSORED RESEARCH

This invention was made with Government support under National Institute of Justice (NIJ) award number 2005-MU-MU-K044. The Government has rights in the claimed inventions.

BACKGROUND

It is often necessary to analyze materials to determine what substances they contain. This is true, for example, in the field of forensic science. Specifically, a forensic scientist may be called upon to analyze a sample from a fire or an explosion that occurred at domicile or place of business. In the case of a fire, the scientist may need to determine whether the fire was accidental or intentional (i.e., arson). In the case of an explosion, the scientist may need to identify explosive materials that were used to cause the explosion to assist law enforcement officials in identifying the individual or organization (e.g., terrorist group) responsible for the explosion.

In the case of fires, determinations as to the cause of the fires are typically made by analyzing fire debris, such as ashes, collected from various locations at the scene of the fire. The debris is placed in a container along with a carbon strip and the container is heated to cause the residue from any substances contained in the debris, such as gasoline or other ignitable liquids, to vaporize and then condense on the carbon strip. The carbon strip is then placed in a solvent to remove the substances and yield a mixture that can be analyzed using a gas chromatograph/mass spectrometer. As the various components from the mixture are output from the gas chromatograph, they are received by the mass spectrometer that breaks each component down and generates a mass spectrum of each component. A total ion chromatogram, which provides an indication of the total quantity, or intensity, of ions present for each component, can be created that comprises a graphic representation of the total ion intensity for each component in time as the components are chromatographically separated.

Once the total ion chromatogram is produced, it can be compared with the total ion chromatograms of various known ignitable liquids that could have been used to start the fire. Normally, such comparison is made by a forensics fire debris analyst familiar with ignitable liquids. Through the comparison, the analyst can draw a conclusion as to what ignitable liquid, if any, started the fire.

The above form of analysis has been used for many years and relies heavily on the expert, but subjective, opinion of the analyst. Furthermore, even when the total ion chromatogram from the sample is very similar to a total ion chromatogram of a suspected ignitable liquid, and it therefore appears likely that the analyst's opinion is correct, it is possible that the similarity could be diminished by the presence of residue formed from other materials which breakdown under the intense heat of a fire (e.g., carpeting, upholstery, foam padding, building materials) to produce substances in the debris that did not arise from the ignitable liquid. That possibility may undermine the conclusions made by the analyst and could result in an inability to prove that arson was in fact the cause of the fire. Moreover, the expert's conclusions are typically only considered valid if each total ion chromatogram used in the analysis was generated using the same equipment under the same conditions, thereby preventing the creation of a central database that could be universally referenced when making determinations as to the substances contained within a sample.

BRIEF DESCRIPTION OF THE FIGURES

The components in the drawings are not necessarily to scale, emphasis instead being placed upon clearly illustrating the principles of the present disclosure. In the drawings, like reference numerals designate corresponding parts throughout the several views.

DETAILED DESCRIPTION

As described above, current analysis performed to identify substances contained in a material, such as a sample pulled from a fire or an explosion scene, are highly reliant on the subjective opinion of a forensics analyst. As described below, however, more objective and more accurate results can be obtained through comparison of summed ion spectra of a sample and known substances. In one embodiment, a summation of all of the ions generated in mass spectral measurements on chromatographed components of a sample, i.e., a summed ion spectrum, is compared with summed ion spectra of various reference substances through the calculation of simple distance and similarity metrics. In the comparison, the analyst can represent data from the sample as a combination of substances to enable more reliable conclusions to be drawn. For example, a fire debris analyst may represent the data from the sample as a combination of an ignitable liquid and other flammable components produced from pyrolysis and/or partial combustion of common background materials, i.e., common materials that are often present at a fire or explosion scene, such as carpeting, upholstery, foam padding, building materials.

Described in the following are various embodiments of systems and methods for identifying substances contained in a material. Although particular embodiments are described, those embodiments are mere example implementations of the systems and methods and it is noted that other embodiments are possible. All such embodiments are intended to fall within the scope of this disclosure. For the purposes of this discussion a "substance" is a material or liquid that is composed of one or more components, and a "component" is a single chemical compound. To cite an example, gasoline may be considered a substance that comprises many different components, including benzene, toluene, dimethyl benzene, and other chemical compounds.

Figure 1:
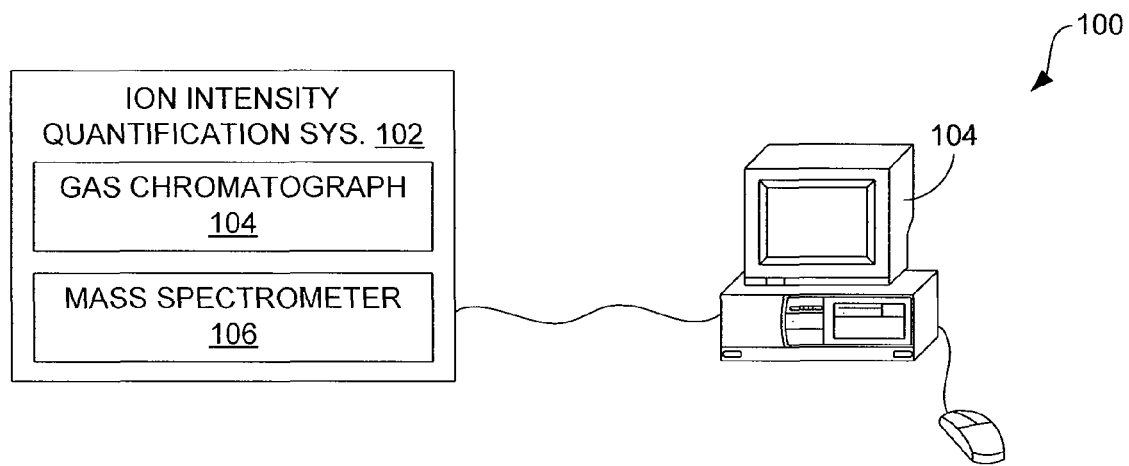
FIG. 1 is a block diagram of an embodiment of a system for identifying substances contained in a material.

FIG. 1 illustrates an example system 100 with which materials can be analyzed to identify substances, such as ignitable liquids or explosive materials, contained in the samples. As indicated in FIG. 1, the system 100 generally comprises an ion intensity quantification system 102 and a computer 104 that are coupled such that data can be sent from the data collection system to the computer. By way of example, the system 100 comprises part of a network, such as a local area network (LAN) or wide area network (WAN).

As its name suggests, the ion intensity quantification system 102 is configured to quantify the ion intensity of ions resulting from compounds, such as those contained in a test sample. In the illustrated embodiment, the ion intensity quantification system 102 comprises a gas chromatograph 104 and a mass spectrometer 106 that together break the components of a given mixture down into various ions. Notably, the gas chromatograph and the mass spectrometer can be combined into a single apparatus (i.e., a GC/MS).

As described below, the computer 104, and more particularly software provided on the computer, is configured to receive the ion intensity information from the ion intensity quantification system 102 and identify possible substances (e.g., ignitable liquids, explosive materials) that may be contained in the sample.

Figure 2:
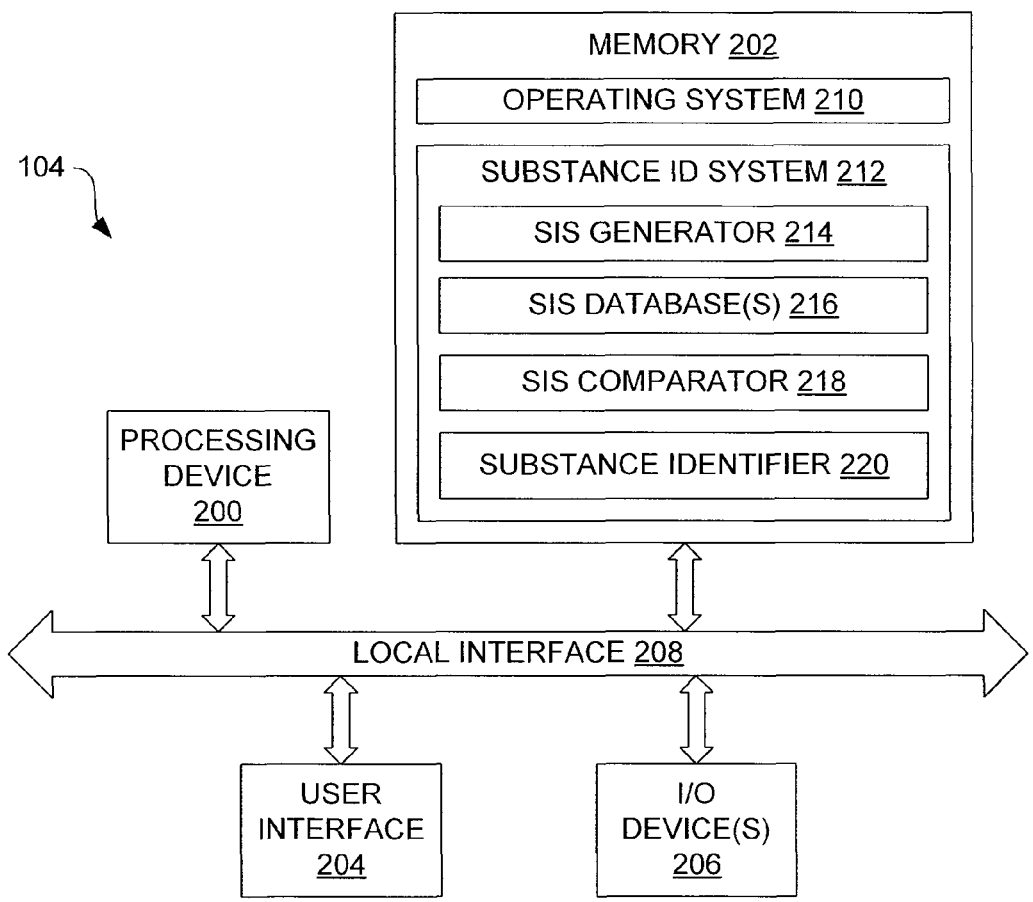
FIG. 2 is a block diagram of an embodiment of a computer shown in FIG. 1.

FIG. 2 is a block diagram illustrating an example architecture for the computer 104 shown in FIG. 1. The computer 104 of FIG. 2 comprises a processing device 200, memory 202, a user interface 204, and at least one I/O device 206, each of which is connected to a local interface 208.

The processing device 200 can include a central processing unit (CPU) or a semiconductor-based microprocessor in the form of a microchip. The memory 202 includes any one of a combination of volatile memory elements (e.g., RAM) and nonvolatile memory elements (e.g., hard disk, ROM, etc.).

The user interface 204 comprises the components with which a user interacts with the computer 104 and therefore may comprise, for example, a keyboard, mouse, and a display. The one or more I/O devices 206 are adapted to facilitate communications with other devices or systems and may include one or more communication components such as a modulator/demodulator (e.g., modem), wireless (e.g., radio frequency (RF)) transceiver, network card, etc.

The memory 202 (i.e., a computer-readable medium) comprises various software programs including an operating system 210 and a substance identification system 212. The operating system 210 controls the execution of other programs and provides scheduling, input-output control, file and data management, memory management, and communication control and related services. As indicated in FIG. 2, the substance identification system 212 comprises various components, including a summed ion spectrum generator 214, one or more summed ion spectra databases 216, a summed ion comparator 218, and a substance identifier 220. Although each of those components are illustrated as being stored on a single computer, it is noted that the components can be distributed over two or more computers.

The summed ion spectrum generator 214 is configured to sum the ion intensities identified by the ion intensity quantification system 102 for all components of test samples.

The one or more summed ion databases 216 comprise one more libraries of summed ion spectra for various substances, such as ignitable liquids, explosive materials, and possible background materials. In some embodiments, the summed ion spectra for the ignitable liquids, explosive materials, and the background materials are maintained in separate databases. In other embodiments, the summed ion spectra for all of the materials are maintained in the same database. Notably, the databases 216 can be stored on a separate computer, such as a server, that can be accessed using a network, such as the Internet.

The summed ion spectra comparator 218 is configured to compare the summed ion spectrum of a test sample with reference summed ion spectra generated with reference to the summed ion spectra of various known substances (e.g., obtained from the databases 216).

Finally, the substance identifier 220 is configured to, relative to the comparison performed by the summed ion spectra comparator 218, identify likely matches between substances contained in a test sample and one or more substances contained in the one or more databases 216.

Various programs (i.e. logic) have been described herein. Those programs can be stored on any computer-readable medium for use by or in connection with any computer-related system or method. In the context of this document, a computer-readable medium is an electronic, magnetic, optical, or other physical device or means that contains or stores a computer program for use by or in connection with a computer-related system or method. Those programs can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In view of the consistency of the mass spectra that are generated for given components, particularly when performing electron ionization at 70 electron-volts (eV), and therefore the uniqueness of the ratios of ions produced for such components, unique combinations of components, for example contained in substances from a test sample, likewise exhibit unique ratios of ions. Therefore, the summed ion spectrum can provide a unique "fingerprint" or "signature" of the sample that can be compared with the summed ion spectra of other substances to identify the substances contained in the test sample with a relatively high degree of accuracy. Examples of such analyses are described in the following.

In the discussions that follow, flow diagrams are provided. It is noted that process steps or blocks in the flow diagrams may represent modules, segments, or portions of code that include one or more executable instructions for implementing specific logical functions or steps in the process. Although particular example process steps are described, alternative implementations are feasible. Moreover, steps may be executed out of order from that shown or discussed, including substantially concurrently or in reverse order, depending on the functionality involved.

Figure 3A:
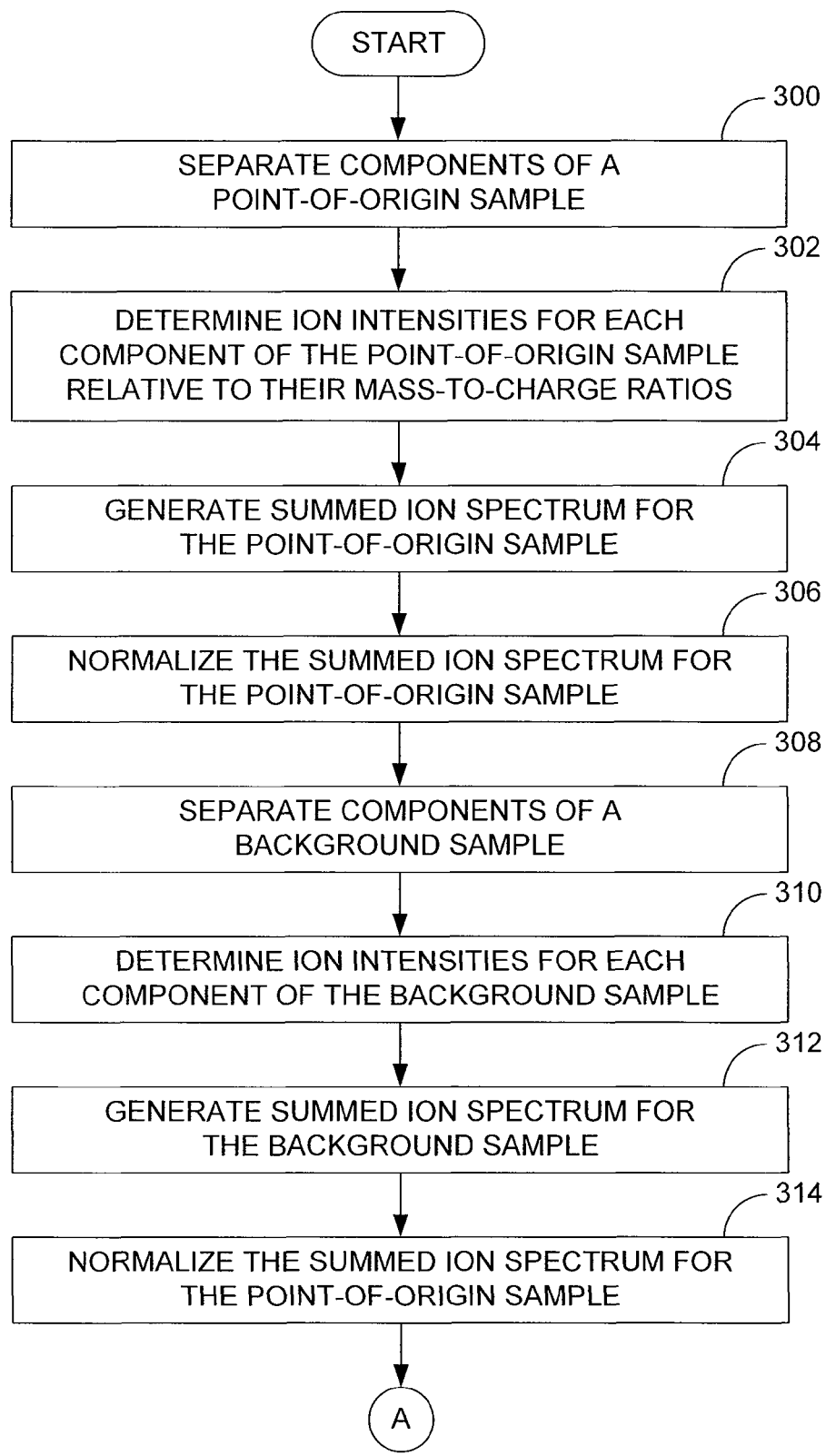
FIGS. 3A and 3B comprise a flow diagram of a first embodiment of a method for identifying substances contained in a material.
Figure 3B:
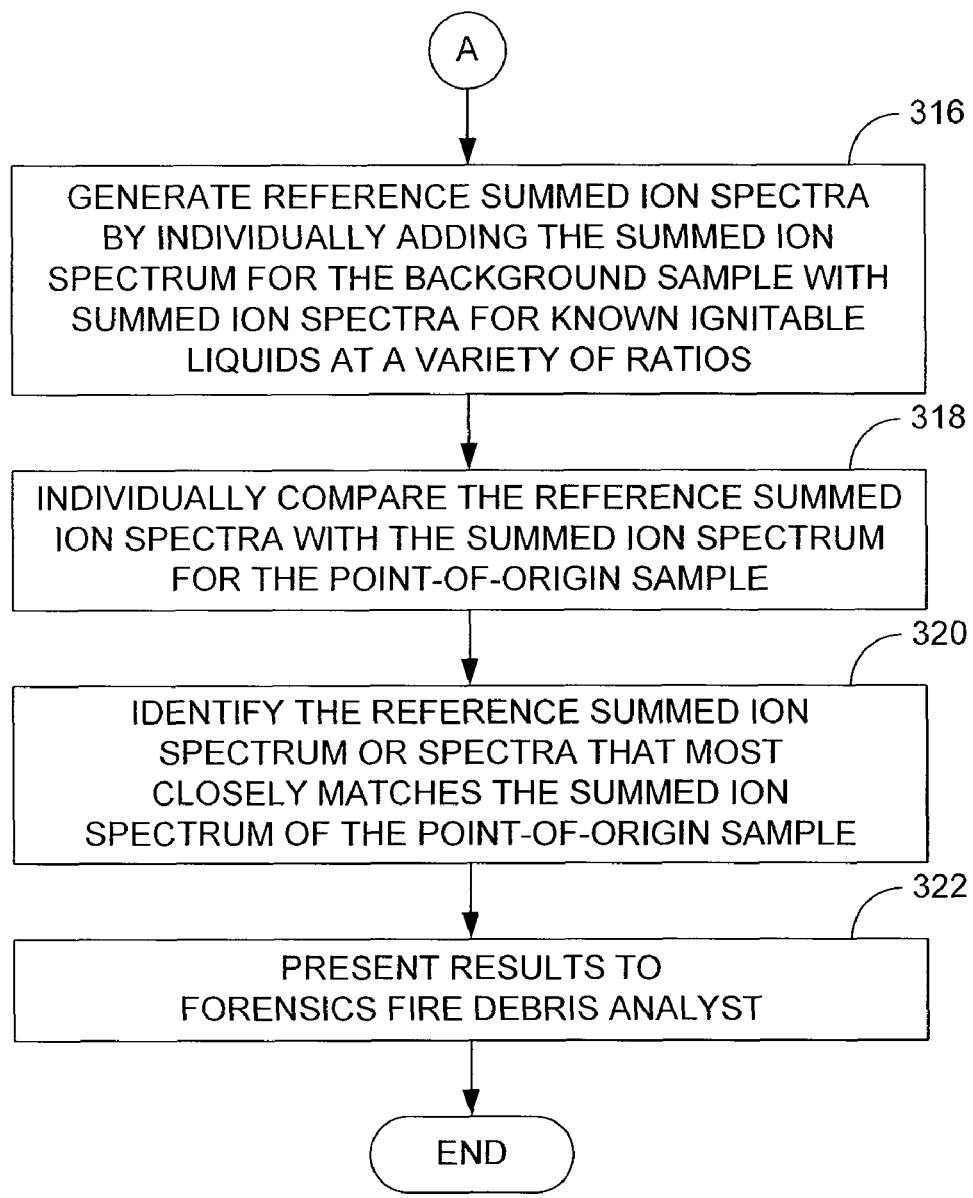

FIGS. 3A and 3B illustrate a first example embodiment of a method for identifying a substance contained in a material. In this example, it is assumed that the material is a point-of-origin sample of debris collected from a fire scene. By "point-of-origin sample," meant is a test sample that is created from substances that were removed from material collected at a suspected point of origin of fire. Furthermore, it is assumed that the analysis to be performed relates to determination as to whether that sample contains one or more ignitable liquids, whose presence may constitute evidence that the fire was intentionally set. Notably, however, the material could be substantially any other material that is to be analyzed for purposes of identifying substances it contains.

Figure 4:
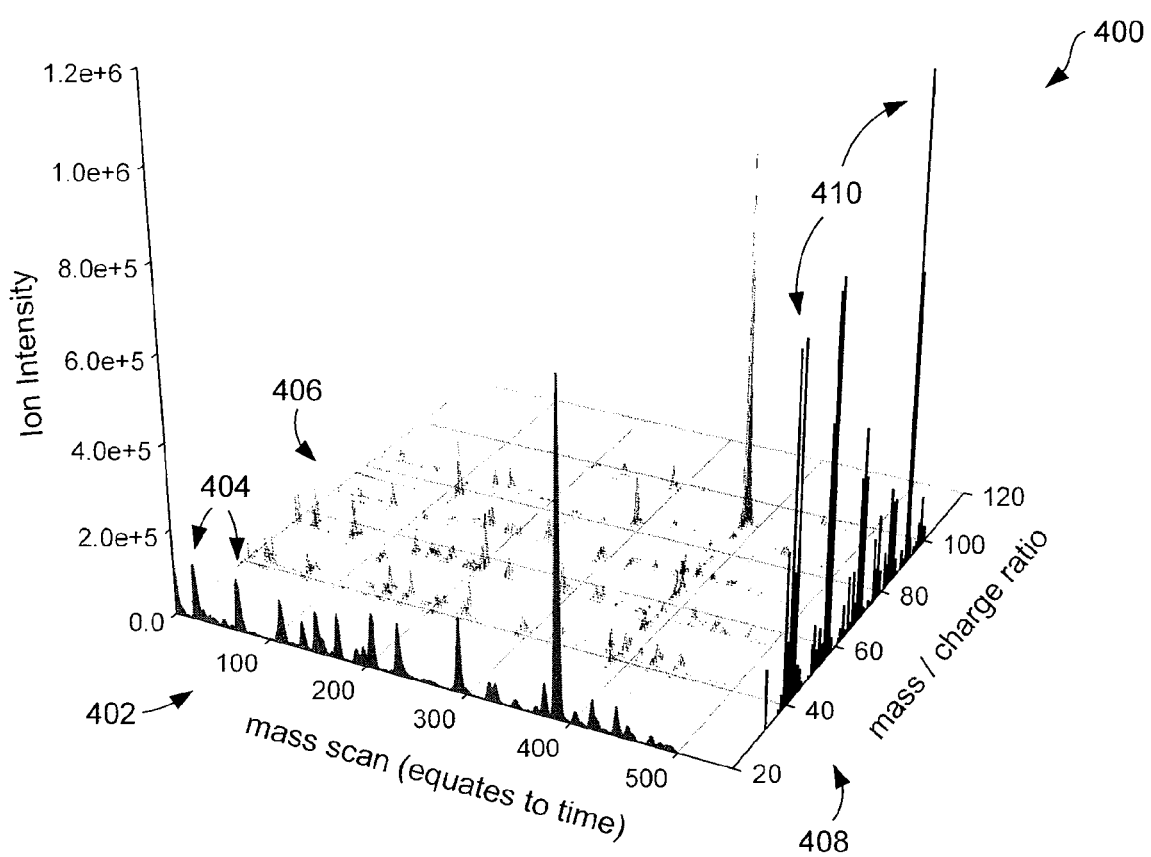
FIG. 4 is a three-dimensional graph that comprises various information regarding an analyzed sample, including the sample's total ion chromatogram, mass spectrum, and summed ion spectrum.

Beginning with block 300 of FIG. 3A, the various components of the point-of-origin sample are separated, for example using a gas chromatograph. During such separation, the various compounds contained within the sample elute at different times, resulting in a total ion chromatogram that plots the total detector response from ions detected as a function of time. The three-dimensional graph 400 of FIG. 4 comprises an example of a total ion chromatogram 402. As indicated in that figure, the total ion chromatogram 402 comprises multiple peaks 404, each pertaining to a different component (and its ions) that has been separated from the sample at a particular point in time.

Next, the ion intensities from each of the components of the point-of-origin sample are determined relative to their mass-to-charge ratios, as indicated in block 302. In that process, the ions of each peak 404 of the total ion chromatogram 402 are analyzed to obtain an indication or representation of the number of ions for each of multiple mass-to-charge ratios. The ion intensities are identified as a function of mass-to-charge ratios in the graph 400 of FIG. 4 as a data set 406 (i.e., the peaks in the center of the x-y plane of the graph). In some embodiments, the ion intensities are determined using a mass spectrometer. In such a case, the various components can be received (e.g., from the gas chromatograph) by an ion source of the mass spectrometer that strips electrons from the component molecules to form positive ions, which then break down into molecular fragments. The fragments that have a positive charge are then accelerated out from the ion source through a mass analyzer of the mass spectrometer, and into a detector that identifies ion intensities as a function of their mass-to-charge ratios.

With reference to block 304, a summed ion spectrum is generated for the point-of-origin sample. In particular, the total ion intensity, which is proportional to the number of ions counted as for each chemical compound, are totaled to yield a spectrum of ion intensities as a function of their mass-to-charge ratios. The graph 400 of FIG. 4 further comprises an example summed ion spectrum 408, which comprises multiple peaks 410 that pertain to various different mass-to-charge ratios between 30 and 100. Each peak 410 represents the total number of ions that have the various mass-to-charge ratios identified along the axis of the spectrum 408. For example, the tallest peak 410 in the summed ion spectrum 408 appears for ions having a mass-to-charge ratio of 91, thereby indicating that there were a greater number of ions having a mass-to-charge ratio of 91 in the sample than any other mass-to-charge ratio. Given that the charge of each ion is +1, the summed ion spectrum 408 may be considered to provide an indication of the total number of ions grouped according to their respective masses.

As a simplified example, assume that a given test sample contained ions having only three different mass-to-charge ratios, i.e., ratios X, Y, and Z. Further assume that the sample comprised only three different components, Components A, B, and C. If the Components A, B, and C had the following ion intensities:

| Component A | Component B | Component C |
|---|---|---|
| X = 100 | X = 50 | X = 100 |
| Y = 50 | Y = 0 | Y = 100 |
| Z = 200 | Z = 100 | Z = 50 | the summed ion spectrum for the sample would be as follows:
X=250
Y=150
Z=350 meaning that sample comprised a total ion intensity of 750, 250 of which had a mass-to-charge ratio X, 150 of which had a mass-to-charge ratio Y, and 350 of which had a mass-to-charge ratio Z.

Returning to FIG. 3A, the summed ion spectrum is normalized, as indicated in block 306, to create a normalized sum ion spectrum. In some embodiments, normalization comprises dividing the intensity for each ion in the summed ion spectrum by the total intensity of all ions in the spectrum. Such normalizing facilitates comparison of the summed ion spectrum with other summed ion spectra, as will be apparent from the following discussion. Continuing with the simplified example, the normalized summed ion spectrum for the test sample would be:
X=0.333
Y=0.200
Z=0.467
which results when each ion intensity (i.e., 250, 150, and 350) is individually divided by the total ion intensity, 750. It is noted that, in other embodiments, normalizing can be performed by dividing the ion intensities by the highest ion intensity. Doing so, however, does not enable the calculation of the distance D described below.

At this point, the same process can be performed in relation to a background sample collected at the fire scene. Specifically, the above process can be performed on burnt material collected from a point outside of the suspected point of origin which is not believed to contain residue from an ignitable liquid. Therefore, components of the background sample can be separated (block 308), ion intensities for the components of the background sample can be determined (block 310), a summed ion spectrum for the background sample can be generated (block 312), and the summed ion spectrum for the background sample can be normalized (block 314). It is noted that, for the remainder of the discussion, references to "summed ion spectra" are actually references to the normalized summed ion spectra. Therefore, the term "normalized" has been omitted for purposes of brevity.

With reference next to block 316 of FIG. 3B, reference summed ion spectra are generated by individually adding the summed ion spectrum for the background sample with summed ion spectra for known ignitable liquids at various different ratios. In some embodiments, the summed ion spectra for known ignitable liquids can be obtained from a summed ion spectrum database. By way of example, the database can comprise a central database, for example hosted by an official governing body (e.g., U.S. government), from which spectra can be downloaded by analysts for the purpose of comparison with their test samples. Addition of the summed ion spectra of the background sample and the known ignitable liquids can be achieved using the following relation:

$$z_N = a * z_{N,IL} + b * z_{N,P}$$ [Equation 1]

where $z_N$ is the resulting reference summed ion spectrum, $z_{N,IL}$ is the summed ion spectrum for a given ignitable liquid, $z_{N,P}$ is the summed ion spectrum for the background sample or pyrolysis, and a and b are variables that sum to one. With Equation 1, the ion intensity for each mass-to-charge ratio of the background sample can be individually summed with the ion intensity for the same mass-to-charge ratios of each known ignitable liquid. With further reference to the simplified example described above, the ion intensity for the mass-to-charge ratio X of the background sample is added to the ion intensity for the mass-to-charge ratio X of a known ignitable liquid, the ion intensity for the mass-to-charge ratio Y of the background sample is added to the ion intensity for the mass-to-charge ratio Y of the known ignitable liquid, and the ion intensity for the mass-to-charge ratio Z of the background sample is added to the ion intensity for the mass-to-charge ratio Z of the known ignitable liquid to generate a new summed ion spectrum. In addition, the relative quantities of the background sample and the ignitable liquids can be varied using variables a and b to take into account possible relative amounts of the background material and an ignitable liquid that may be present in the point-of-origin sample. For example, when a=0.1 and b=0.9, the resulting reference summed ion spectrum relates to a hypothetical mixture that comprises 10% of the ignitable liquid and 90% of the background sample. In some embodiments, a and b can each comprise a value between 0 and 1.0 that sum to one. By way of example, if increments of 0.1 are used and the zero cases are excluded, there will be 9 total variations are generated for each reference combination (i.e., ratios of 1:9, 2:8, 3:7, 4:6, 5:5, 6:4, 7:3, 8:2, 9:1). Of course a greater or lesser number of variations can be considered. Moreover, if desired, the summed ion spectrum of the background material can be combined with the summed ion spectra of more than one ignitable liquid. In such a case, Equation 1 would be modified to include multiple ignitable liquids (i.e., $z_{N,IL}$ values) more than two variables that sum to one.

Through the process described in relation to block 316, multiple reference summed ion spectra are produced that emulate mixtures of background material found at the fire scene and ignitable liquids that potentially may have been used to start the fire, at various different ratios. The number of reference summed ion spectra that are created depends upon the number of known ignitable liquids and the number of ratios. In a typical case, however, hundreds or thousands of reference summed ion spectra will be generated. If one of those reference summed ion spectra substantially matches the point-of-origin sample, which presumably contains the same background material and an ignitable liquid, it may be assumed with relative certainty that the point-of-origin sample contains the same ignitable liquid that was used to produce the matching reference summed ion spectrum.

Once the various reference summed ion spectra have been formed, or as those reference summed ion spectra are formed, each reference summed ion spectrum is individually compared with the summed ion spectrum for the point-of-origin sample, as indicated in block 318. In some embodiments, such comparison can be achieved using the following relation:

$$D = \frac{\sum_i |z_{N1}(i) - z_{N2}(i)|}{2} \qquad [\text{Equation 2}]$$

where D is the mathematical "distance" between the reference summed ion spectrum and the point-of-origin summed ion spectrum, $z_{N1}(i)$ is the point-of-origin summed ion spectrum, and $z_{N2}(i)$ is the reference summed ion spectrum. With such an relation, a perfect match between the reference summed ion spectrum and the point-of-origin summed ion spectrum will yield a zero in the numerator and D=0, while a perfect mismatch (i.e., complete opposites) will yield a 2 in the numerator and D=1. Regardless, using the above process, a value for D is generated for each reference summed ion spectrum.

Next, as indicated in block 320, the reference summed ion spectrum or spectra that most closely matches the summed ion spectrum of the point-of-origin sample is/are identified. By way of example, the reference summed ion spectra that yield the smallest values for D can be selected as the most likely candidates. Regardless, the results can then be presented to a forensics fire debris analyst for consideration, as indicated in block 322. If desired, the distance, D, can first be converted into a mathematical similarity, S, which may be more intuitive for the analyst or persons to which the analyst may need to explain the results. Such conversion may be achieved using the following relation:

$$S = 1 - D \qquad [\text{Equation 3}]$$

Using that relation, a value of S=1 identifies a perfect match, while a value of S=0 identifies a perfect mismatch.

Figure 5:
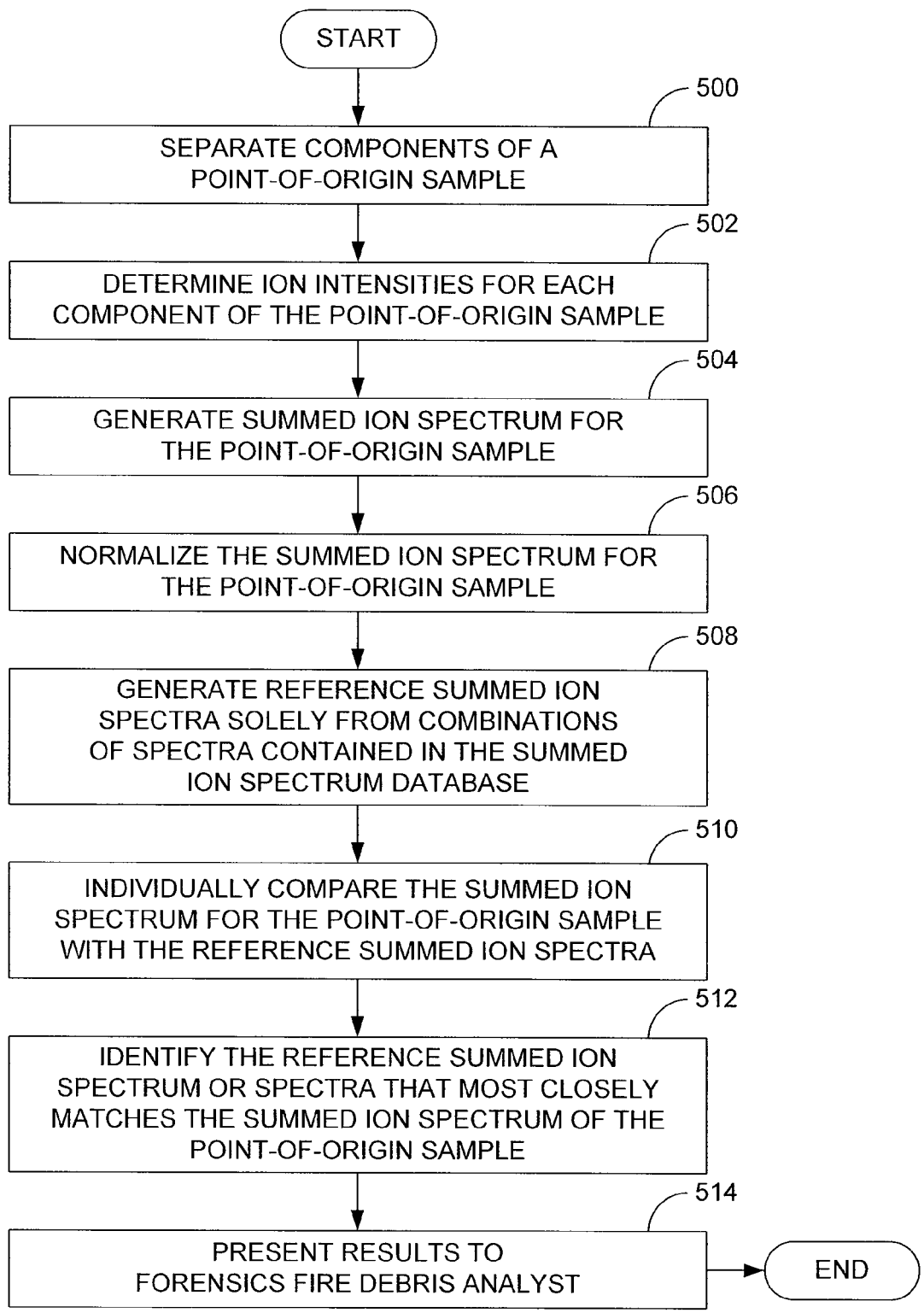
FIG. 5 is a flow diagram of second embodiment of a method for identifying substances contained in a material.

FIG. 5 presents a second example embodiment of a method for identifying a substance contained in a material. Again, it is assumed for the purposes of this discussion that the material is a sample of fire debris and that the analysis to be performed relates to determination as to whether that sample contains an ignitable liquid. Furthermore, for the purposes of FIG. 5, it is assumed that a summed ion spectra database, for example a central database, has been created that contains not only summed ion spectra for known ignitable liquids but also summed ion spectra for pyrolysis or partial combustion of common background materials (e.g., carpeting, upholstery, foam padding, building materials).

The method illustrated in FIG. 5 begins in similar manner to the method described above in relation to FIGS. 3A and 3B. Therefore, components of the point-of-origin sample can be separated (block 500), ion intensities for the components can be determined (block 502), a summed ion spectrum for the point-of-origin sample can be generated (block 504), and the summed ion spectrum can be normalized (block 506).

Once the normalized summed ion spectrum, or just "summed ion spectrum," for the point-of-origin sample has been generated, that spectrum can be compared with reference summed ion spectra. Instead of generating the reference summed ion spectra by analyzing a background sample taken from the fire scene as in the method of FIGS. 3A and 3B, however, the reference summed ion spectra are generated solely from combinations of spectra contained in the database, as indicated in block 508. More particularly, the reference summed ion spectra are generated through various combinations of known background materials and ignitable liquids. For example, the reference summed ion spectra can comprise combinations of a single background material and a single ignitable liquid. Alternatively, the reference summed ion spectra can comprise combinations of multiple background materials and one or more ignitable liquids. As above, various ratios of materials and/or liquids can be considered and multiple (e.g., hundreds or thousands) of reference summed ion spectra may result. Once the reference summed ion spectra have been generated, they can be compared to the summed ion spectrum, as indicated in block 510. Through such comparison, the reference summed ion spectrum or spectra that most closely matches the summed ion spectrum of the point-of-origin sample is identified (block 512), and results can be presented to a forensics fire debris analyst for consideration (block 514).

From the foregoing, it can be appreciated that disclosed systems and methods enable forensic analysts to rapidly identify substances contained in a sample. In particular, the analyst can compare the summed ion spectrum of a test (e.g., point-of-origin) sample with reference summed ion spectra resulting from combinations of various flammable components. As mentioned above, the systems and methods further enable the creation of a central database that contains summed ion spectra that can be made available to analysts to facilitate the identification of such substances. This is possible given that, unlike a total ion chromatogram, the summed ion spectrum for a given substance will be substantially identical irrespective of the apparatus (e.g., gas chromatograph) used and the conditions (e.g., rate of temperature rise) under which the analysis is performed. In other words, the same chemicals produce the same mass spectrum irrespective of the time at which they elute. Such consistency further may enable analysts to add summed ion spectra obtained from their analyses in their own laboratories to the database to expand its breadth. Regardless, a centralized database could be used in similar manner to the fingerprint database maintained by the FBI because the summed ion spectrum of each substance is unique.

It is noted that the disclosed systems and methods can include further additions, including a methodology to account for ignitable liquid evaporation resulting in chromatographic distortions, the use of target factor analysis to aid in the identification of ignitable liquids in the presence of pyrolysis/combustion products, calculation of similarity and distance from covariance mapping of the GC-MS data, and enhanced graphic display of the covariance maps and total ion chromatograms.

Although several of the discussions of the present disclosure have focused on fire scenes and identification of ignitable liquids, the systems and methods are in no way limited to such applications. Therefore, the methodologies disclosed herein can be extended to explosion sites and explosive materials. In such a case, the type of explosives used to cause an explosion and, potentially, the individual or organization that planted and detonated an explosive device, may be determined. Indeed, since the summed ion spectrum for any unique mixture is likewise unique, the approach may also be useful for substantially any application in which identification of certain substances within a sample may be useful. Examples of such applications include identifying or discriminating between illicit drugs coming from the same or different batches/manufacturers, identifying individuals based on the composition of finger print chemicals or odor signatures, identifying signature patterns relating to medical conditions based on the analysis of a complex mixture rather than separation and identification of a single molecule responsible for a disease or condition, and rapid industrial screening of complex products comprised of mixtures for the purpose of quality assurance and process control.

Finally, it is noted that, although the use of a gas chromatograph has been described, it is possible, at least in some embodiments, to instead use a liquid chromatograph.

The invention claimed is:

1. A method for identifying substances, the method comprising:
    generating a summed ion spectrum for a test sample, the summed ion spectrum identifying ion intensities at multiple different mass-to-charge ratios;
    generating a plurality of reference summed ion spectra for comparison with the summed ion spectrum of the test sample, each reference summed ion spectrum comprising a combined summed ion spectrum that is created by adding the summed ion spectrum of a first substance with the summed ion spectrum of a second substance such that each reference summed ion spectrum comprises the combined summed ion intensities of at least two substances;
    individually comparing the summed ion spectrum of the test sample with each of the reference summed ion spectra to identify a potential match; and
    identifying the reference summed ion spectrum or spectra that most closely matches or match the summed ion spectrum of the test sample.

2. The method of claim 1, further comprising, prior to generating a summed ion spectrum for the test sample, separating components of the test sample.

3. The method of claim 2, wherein separating components of the test sample comprises separating the components using a chromatograph.

4. The method of claim 2, further comprising, prior to generating a summed ion spectrum for the test sample, determining the ion intensities of the test sample.

5. The method of claim 4, wherein determining the ion intensities of the test sample comprises determining the ion intensities using a mass spectrometer.

6. The method of claim 1, further comprising, prior to comparing the summed ion spectrum of the test sample with each of the reference summed ion spectra, normalizing the summed ion spectrum of the test sample and each of the reference summed ion spectra.

7. The method of claim 6, wherein normalizing the summed ion spectrum of the test sample and each of the reference summed ion spectra comprises dividing the individual ion intensities at each mass-to-charge ratio of by a total ion intensity.

8. The method of claim 1, wherein generating the reference summed ion spectra comprises generating at least one reference summed ion spectrum that combines the summed ion spectrum of a further sample with the summed ion spectra of multiple different substances.

9. The method of claim 1, wherein identifying the reference summed ion spectrum or spectra that most closely matches or match the summed ion spectrum of the test sample comprises calculating a mathematical distance between each reference summed ion spectrum and the summed ion spectrum of the test sample.

10. The method of claim 9, wherein identifying the reference summed ion spectrum or spectra that most closely matches or match the summed ion spectrum of the test sample further comprises using the mathematical distance to calculate a mathematical similarity between each reference summed ion spectrum and the summed ion spectrum of the test sample.

11. A computer-readable medium that stores a substance identification system comprising:
    logic configured to generate a summed ion spectrum for a test sample, the summed ion spectrum identifying ion intensities at multiple different mass-to-charge ratios;
    logic configured to generate a plurality of reference summed ion spectra for comparison with the summed ion spectrum of test sample, each reference summed ion spectrum comprising a combined summed ion spectrum that is created by adding the summed ion spectrum of a first substance with the summed ion spectrum of a second substance such that each reference summed ion spectrum comprises the combined summed ion intensities of at least two substances;
    logic configured to individually compare the summed ion spectrum of the test sample with each of the reference summed ion spectra to identify a potential match; and
    logic configured to identify the reference summed ion spectrum or spectra that most closely matches or match the summed ion spectrum of the test sample.

12. The computer-readable medium of claim 11, wherein the logic configured to generate the reference summed ion spectra comprises logic configured to generate at least one reference summed ion spectrum that combines the summed ion spectrum of a further sample with the summed ion spectra of multiple different substances.

13. The computer-readable medium of claim 11, wherein the logic configured to identify the reference summed ion spectrum or spectra that most closely matches or match the summed ion spectrum of the test sample comprises logic configured to calculate a mathematical distance between each reference summed ion spectrum and the summed ion spectrum of the test sample.

14. The computer-readable medium of claim 13, wherein the logic configured to identify the reference summed ion spectrum or spectra that most closely matches or match the summed ion spectrum of the test sample further comprises logic configured to use the mathematical distance to calculate a mathematical similarity between each reference summed ion spectrum and the summed ion spectrum of the test sample.

15. A computer comprising:
 a processing device; and
 memory that stores a central database comprising summed ion spectra, each summed ion spectrum comprising a combination of a summed ion spectrum for a first substance and the summed ion spectrum of a second substance, each of the summed ion spectra comprising ion intensities at multiple different mass-to-charge ratios, the central database being accessible for comparison with test samples to assist analysts in identifying possible substances contained in the test samples.

16. A method for identifying a substance that may have caused a fire or explosion at a scene of the fire or explosion, the method comprising:
 collecting a point-of-origin sample from a suspected point of origin of the fire or explosion;
 collecting a background sample from a location at the scene not suspected to be the point of origin of the fire or explosion;
 generating a summed ion spectrum for the point-of-origin sample, the summed ion spectrum identifying ion intensities at multiple different mass-to-charge ratios;
 generating a plurality of reference summed ion spectra for comparison with the summed ion spectrum of the point-of-origin sample, each reference summed ion spectrum comprising a combined summed ion spectrum that is created by generating a summed ion spectrum for the background sample and adding to that summed ion spectrum a summed ion spectrum for a substance that could have been used to cause the fire or explosion, such that the reference summed ion spectra each comprises the combined summed ion intensities of the background sample and a substance that could have been used to cause the fire or explosion;
 individually comparing the summed ion spectrum of the point-of-origin sample with each of the reference summed ion spectra to identify a potential match; and
 identifying the reference summed ion spectrum or spectra that most closely matches or match the summed ion spectrum of the point-of-origin sample.

17. The method of claim 16, wherein generating the reference summed ion spectra comprises generating at least one reference summed ion spectrum that combines the summed ion spectrum of the background sample with the summed ion spectra of multiple different substances that could have been used to cause the fire or explosion.

18. The method of claim 16, wherein identifying the reference summed ion spectrum or spectra that most closely matches or match the summed ion spectrum of the point-of-origin sample comprises calculating a mathematical distance between each reference summed ion spectrum and the summed ion spectrum of the point-of-origin sample.

19. The method of claim 16, wherein generating a plurality of reference summed ion spectra comprises, for each reference summed ion spectrum, applying a separate weighting factor to each of the summed ion spectrum of the background sample and the summed ion spectrum of the substance that could have been used to cause the fire or explosion prior to adding those summed ion spectra together to take into account possible relative quantities of substances that might be present in the point-of-origin sample.

20. The method of claim 19, wherein the weighting factors sum to one.

21. The method of claim 19, wherein generating a plurality of reference summed ion spectra further comprises varying the weighting factors to vary the possible relative quantities.

22. A computer-readable medium that stores a substance identification system comprising:
 logic configured to generate a summed ion spectrum for a point-of-origin sample obtained from a suspected point of origin of a fire or explosion at a scene of the fire or explosion, the summed ion spectrum identifying ion intensities at multiple different mass-to-charge ratios;
 logic configured to generate a plurality of reference summed ion spectra for comparison with the summed ion spectrum of point-of-origin sample, each reference summed ion spectrum comprising a combined summed ion spectrum that is created by generating a summed ion spectrum for a background sample obtained from a location at the scene not suspected to be the point of origin of the fire or explosion and adding to that summed ion spectrum a summed ion spectrum for a substance that could have been used to cause the fire or explosion, such that the reference summed ion spectra each comprises the combined summed ion intensities of the background sample and a substance that could have been used to cause the fire or explosion;
 logic configured to individually compare the summed ion spectrum of the point-of-origin sample with each of the reference summed ion spectra to identify a potential match; and
 logic configured to identify the reference summed ion spectrum or spectra that most closely matches or match the summed ion spectrum of the point-of-origin sample.

23. The computer-readable medium of claim 22, wherein the logic configured to generate the reference summed ion spectra comprises logic configured to generate at least one reference summed ion spectrum that combines the summed ion spectrum of the background sample with the summed ion spectra of multiple different substances that could have been used to cause the fire or explosion.

24. The computer-readable medium of claim 22, wherein the logic configured to identify the reference summed ion spectrum or spectra that most closely matches or match the summed ion spectrum of the point-of-origin sample comprises logic configured to calculate a mathematical distance between each reference summed ion spectrum and the summed ion spectrum of the point-of-origin sample.

25. The computer-readable medium of claim 22, wherein the logic configured to generate a plurality of reference summed ion spectra comprises logic configured to, for each reference summed ion spectrum, apply a separate weighting factor to each of the summed ion spectrum of the background sample and the summed ion spectrum of the substance that could have been used to cause the fire or explosion prior to adding those summed ion spectra together to take into account possible relative quantities of substances that might be present in the point-of-origin sample.

26. The computer-readable medium of claim 25, wherein the weighting factors sum to one.

27. The computer-readable medium of claim 25, wherein the logic configured to generate a plurality of reference summed ion spectra is further configured to vary the weighting factors to vary the possible relative quantities.

* * * * *